(12) United States Patent
Kohrs

(10) Patent No.: US 6,855,166 B2
(45) Date of Patent: Feb. 15, 2005

(54) INTEVERTEBRAL IMPLANT WITH REDUCED CONTACT AREA AND METHOD

(75) Inventor: Douglas W. Kohrs, Edina, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 0 days.

(21) Appl. No.: 09/777,631

(22) Filed: Feb. 6, 2001

(65) Prior Publication Data

US 2001/0011191 A1 Aug. 2, 2001

Related U.S. Application Data

(63) Continuation of application No. 09/045,213, filed on Mar. 20, 1998, now Pat. No. 6,224,631.

(51) Int. Cl.⁷ .................................................. A61F 2/44
(52) U.S. Cl. .................................................. 623/17.11
(58) Field of Search ........................... 623/17.11, 17.15, 623/17.16, 17.13, 17.14

(56) References Cited

U.S. PATENT DOCUMENTS

| | | |
|---|---|---|
| 2,677,369 A | 5/1954 | Knowles |
| 4,349,921 A | 9/1982 | Kuntz |
| 4,501,269 A | 2/1985 | Bagby |
| 4,743,256 A | 5/1988 | Brantigan |
| 4,834,757 A | 5/1989 | Brantigan |
| 4,878,915 A | 11/1989 | Brantigan |
| 4,936,848 A | 6/1990 | Bagby |

(List continued on next page.)

FOREIGN PATENT DOCUMENTS

| | | |
|---|---|---|
| CA | 2229714 | 5/1997 |
| DE | 196 30 256 A1 | 1/1998 |
| EP | 0 425 542 B1 | 3/1995 |
| FR | 2 703 580 | 10/1994 |
| SU | 1007661 A | 3/1983 |
| WO | WO 87/07827 | 12/1987 |
| WO | WO 96/22747 | 8/1996 |
| WO | WO 97/15247 | 5/1997 |
| WO | WO 98/48738 | 11/1998 |
| WO | WO 00/35389 | 6/2000 |

Primary Examiner—Bruce E Snow
(74) Attorney, Agent, or Firm—Faegre & Benson LLP

(57) ABSTRACT

The disclosure provides fusion implants, instruments and methods for insertion of the implants between opposing vertebral bodies to facilitate stabilization or arthrodesis of an intervertebral joint. A cross section through the longitudinal dimension of the implant is substantially configured in an "I" shape. In addition to other features, the implants of the invention provide a reduced contact surface area with the interior surface of a bore formed for receiving the implant.

23 Claims, 8 Drawing Sheets

U.S. PATENT DOCUMENTS

| | | |
|---|---|---|
| 4,961,740 A | 10/1990 | Ray et al. |
| 5,015,247 A | 5/1991 | Michelson |
| 5,026,373 A | 6/1991 | Ray et al. |
| 5,055,104 A | 10/1991 | Ray |
| 5,062,850 A | 11/1991 | MacMillan et al. |
| 5,147,402 A | 9/1992 | Bohler et al. |
| 5,192,327 A | 3/1993 | Brantigan |
| 5,294,391 A | 3/1994 | McMillin |
| 5,425,772 A | 6/1995 | Brantigan |
| 5,443,514 A | 8/1995 | Steffe |
| 5,458,638 A | 10/1995 | Kuslich et al. |
| 5,484,437 A | 1/1996 | Michelson |
| 5,489,307 A | 2/1996 | Kuslich et al. |
| 5,489,308 A | 2/1996 | Kuslich et al. |
| 5,505,732 A | 4/1996 | Michelson |
| 5,554,191 A | 9/1996 | Lahille et al. |
| 5,562,738 A | 10/1996 | Boyd et al. |
| 5,593,409 A | 1/1997 | Michelson |
| 5,609,635 A | 3/1997 | Michelson |
| 5,609,636 A | 3/1997 | Kohrs et al. |
| 5,645,598 A | 7/1997 | Brosnahan, III |
| 5,653,763 A | 8/1997 | Errico et al. |
| 5,658,337 A | 8/1997 | Kohrs et al. |
| 5,665,122 A | 9/1997 | Kambin |
| 5,669,909 A | 9/1997 | Zdeblick et al. |
| 5,741,253 A | 4/1998 | Michelson |
| 5,865,847 A | 2/1999 | Kohrs et al. |
| 5,885,287 A | 3/1999 | Bagby |
| 5,888,227 A | 3/1999 | Cottle |
| 5,888,228 A | 3/1999 | Knothe et al. |
| 5,897,593 A | 4/1999 | Kohrs et al. |
| 5,904,719 A * | 5/1999 | Errico et al. .................. 623/17 |
| 5,906,616 A | 5/1999 | Pavlov et al. |
| 5,984,922 A | 11/1999 | McKay |
| 6,080,155 A | 6/2000 | Michelson |
| 6,120,506 A | 9/2000 | Kohrs et al. |
| 6,143,420 A * | 11/2000 | McKay ........................ 623/17 |
| 6,165,219 A | 12/2000 | Kohrs et al. |
| 6,224,631 B1 * | 5/2001 | Kohrs ..................... 623/17.11 |

\* cited by examiner

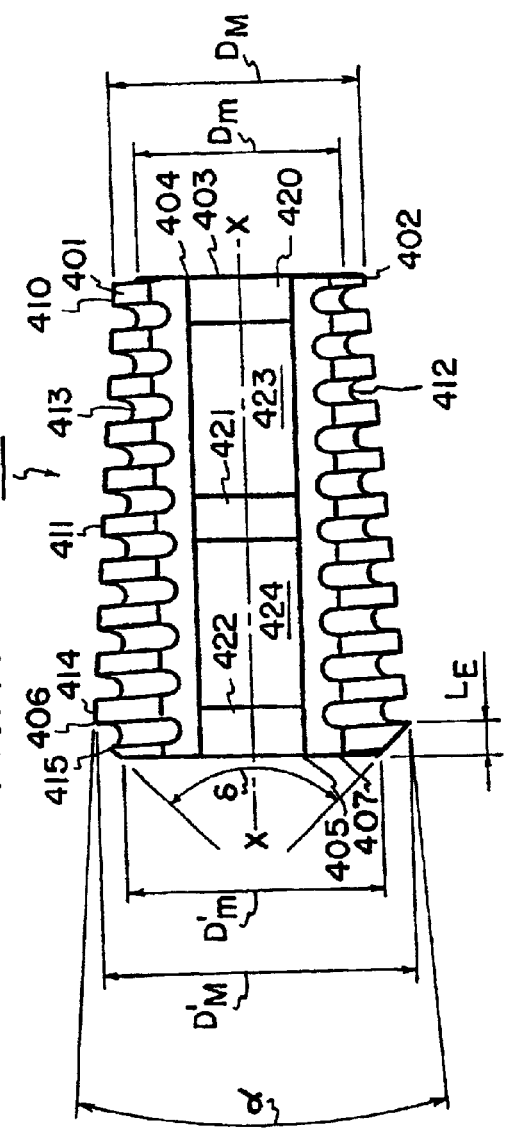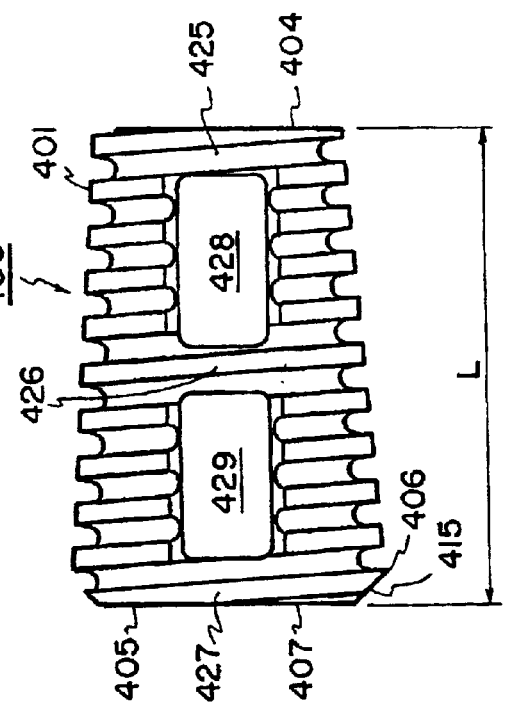

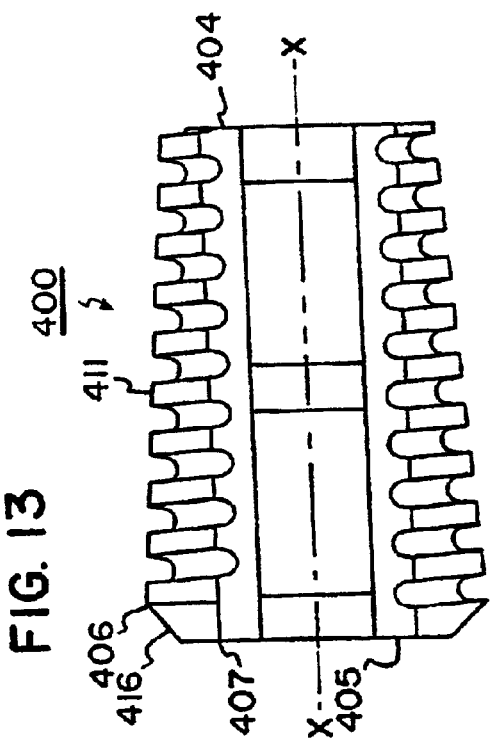
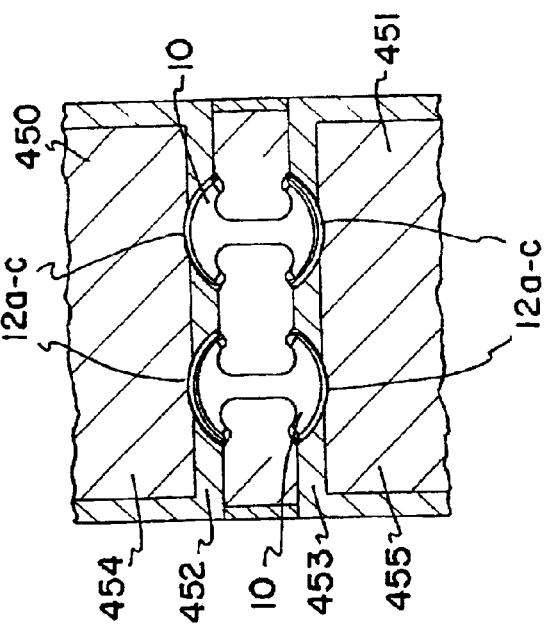

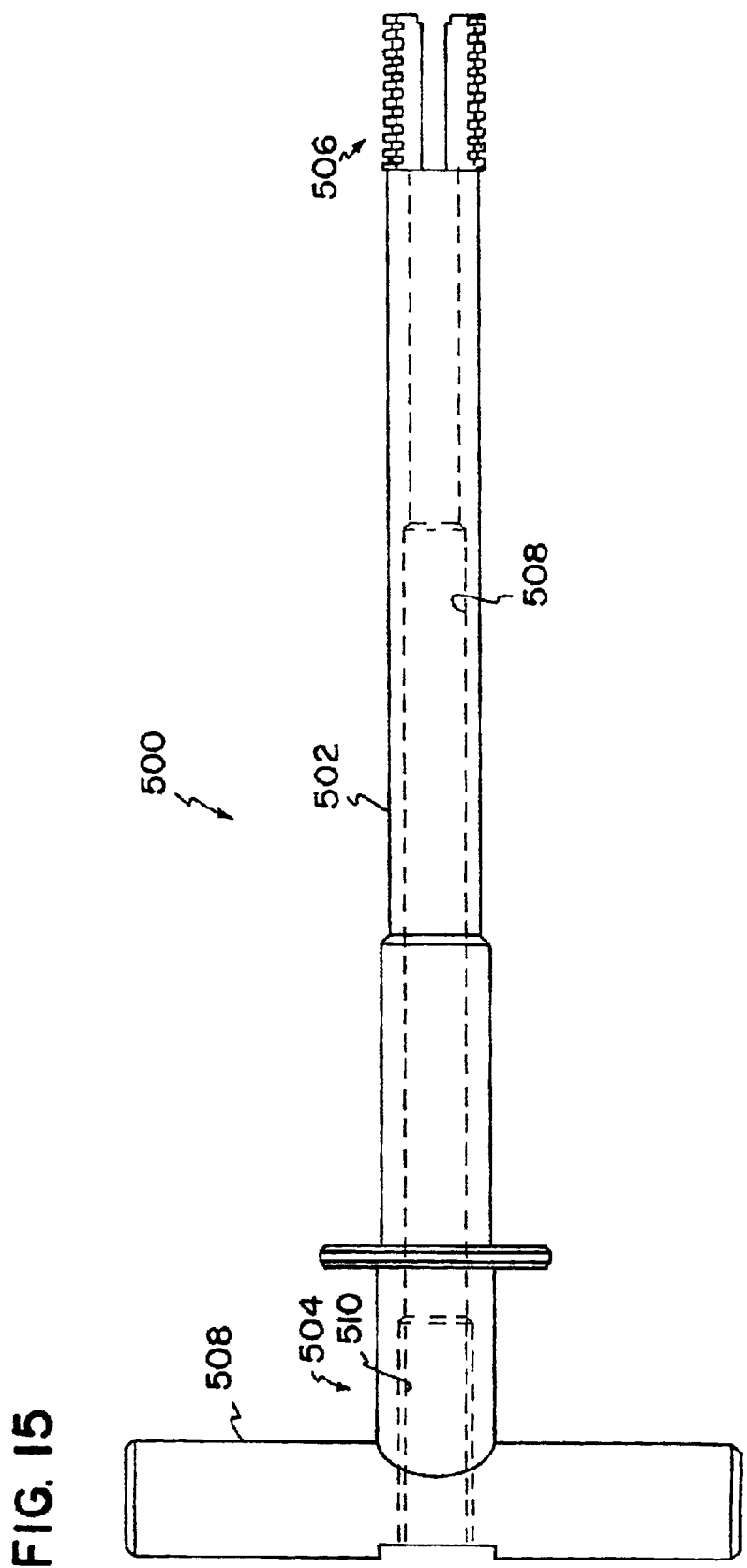

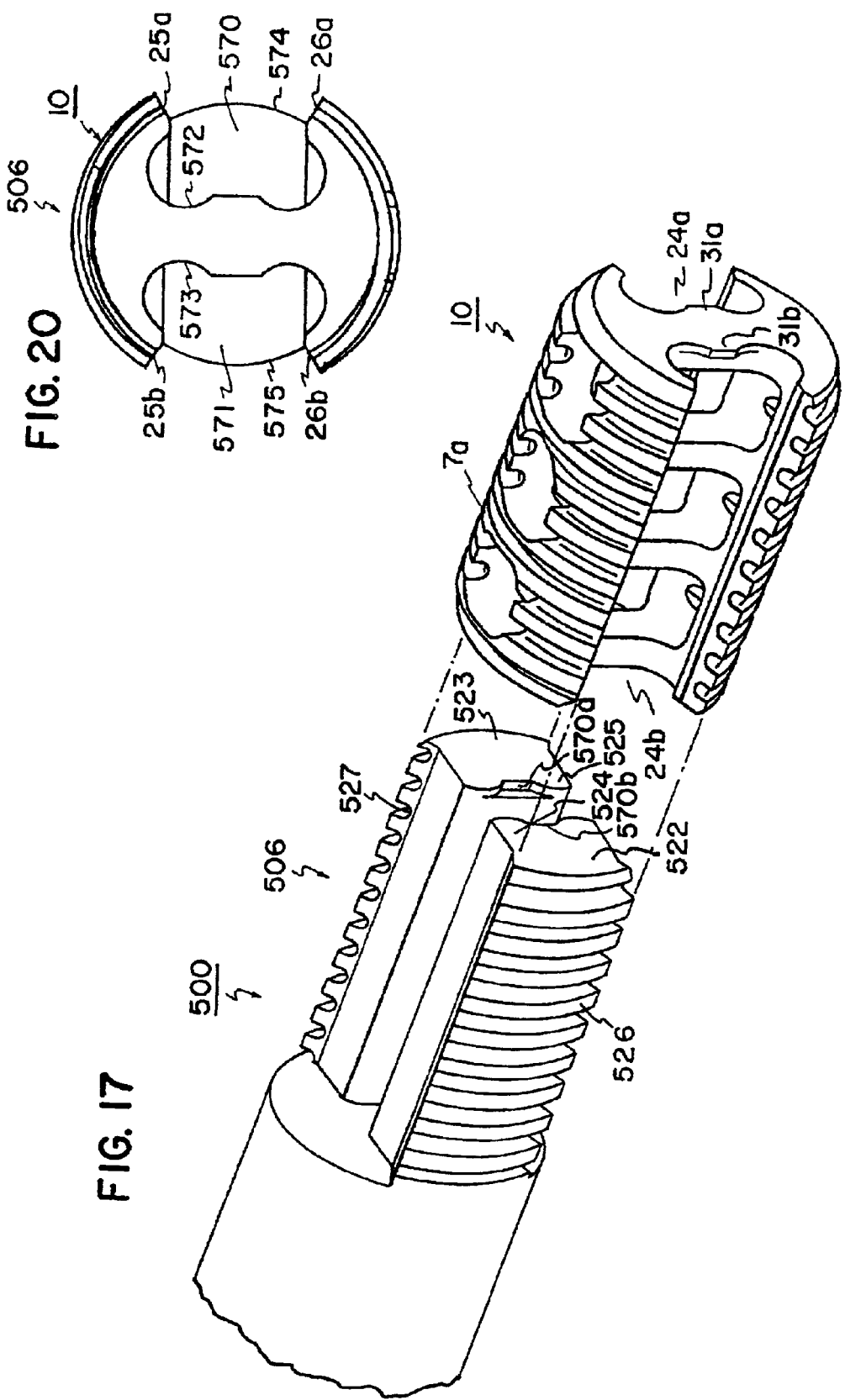

INTEVERTEBRAL IMPLANT WITH REDUCED CONTACT AREA AND METHOD

Cross-Reference to Related Applications

The present application is a continuation application of U.S. Ser. No. 09/045,213 filed Mar. 20, 1998, now U.S. Pat. No. 6,224,631 which application is incorporated herein by reference.

FIELD OF THE INVENTION

This invention pertains to procedures for intervertebral stabilization. Specifically, the disclosure provides implants, instrumentation and methods to facilitate stabilization or fusion between two vertebrae.

BACKGROUND OF THE INVENTION

Chronic back problems cause pain and disability for a large segment of the population. Frequently, the cause of back pain is traceable to diseased disk material between opposing vertebrae. When the disk material is diseased, the opposing vertebrae may be inadequately supported, resulting in persistent pain.

Surgical techniques have been developed to remove the diseased disk material and fuse the joint between opposing vertebral bodies. Stabilization and/or arthrodesis of the intervertebral joint can reduce the pain associated with movement of an intervertebral joint having diseased disk material. Generally, fusion techniques involve removal of the diseased disk and packing the void area with a suitable matrix for facilitating a bony union between the opposing vertebral bodies. Surgical devices for facilitating interbody fusion have also been developed. These devices typically provide for maintaining appropriate intervertebral spacing and stabilization of the vertebrae during the fusion process. Generally, these devices are referred to as cages. Examples of such devices are disclosed in, for example, U.S. Pat. Nos. 5,458,638, 5,489,307, 5,055,104, 5,026,373, 5,015,247, 4,961,740, 4,743,256 and 4,501,269, the entire disclosures of which are incorporated herein by reference.

Generally, the fusion device is implanted within a site prepared between opposing vertebrae. Typically, the site is a bore formed in the disk material and extends through the cortical end plates and into the cancellous bone of the opposing vertebrae. Many of the present fusion devices have a chamber enclosed by a cylindrical or rectangular wall that substantially contacts the entire interior surface of the bore. After placement of the device into the bore, the enclosed chamber (interior of the cage) can be filled with bone chips or other suitable material for facilitating bony union between the vertebrae.

Most of the present fusion devices provide vertebral stabilization during the fusion process by contact of the entire outer wall of the fusion device with substantially the entire interior surface of the wall of the insertion bore. While support provided by contact of the device with the entire wall of the bore provides adequate vertebral stabilization during the fusion process, it also has many disadvantages. For example, the greater the overall contact area of the device with the surface of the bore, the slower the rate at which new bone can grow into the bore to stabilize the joint. In addition, the greater the surface area of the device that contacts the surface area of the bore, the less continuity that can occur between the bone that is external to the device and the bone that is internal to the device. This lack of continuity of bone can translate into reduced structural integrity of the bony union. Furthermore, reducing the amount and continuity of the bone growth into the fusion site can cause the patient's body to rely on the device for long term stabilization rather than relying on the structural integrity of the new bony union. The potential orthopedic problems resulting from the body's reliance on orthopedic implants for structural support are well known.

Moreover, because most fusion devices are manufactured with materials that are radiopaque to typical diagnostic imaging modalities, assessment of the status of new bone growth during the fusion process can be limited.

Accordingly, there is a continuing need for improved intervertebral stabilizing devices and methods. The present invention is directed to addressing these needs.

SUMMARY OF THE INVENTION

The invention is directed to procedures for intervertebral stabilization of opposing vertebrae. The disclosure provides implants, instruments and methods for stabilization or fusion of opposing vertebrae.

At various locations throughout the specification, lists of examples are provided. It should be noted that the examples are provided for illustrative purposes and are not intended to limit the scope of the invention.

An implant according to the invention includes an implant body having a first and second end spaced apart by a longitudinal axis of the implant. The implant body includes a first transverse member and a second transverse member maintained in spaced apart relationship by a central support member. The transverse members each include a bearing surface oriented to contact opposing vertebral surfaces.

The bearing surfaces of the implant can be linear, curved or other suitable configuration. In addition, the bearing surfaces can include a pattern for anchoring the implant and/or resisting displacement once the implant is inserted between opposing vertebrae.

An implant of the invention provides a reduced displacement volume relative to the insertion bore necessary to accommodate the implant. The central support member or transverse members can also include openings which further reduce the displacement volume of the implants. In addition to enhancing the continuity of the new bone growth between the stabilized vertebral bodies, the reduced displacement volume of the implant facilitates assessment of the fusion process using known imaging modalities.

BRIEF DESCRIPTION OF THE DRAWINGS

FIG. 11 is a side elevation view of an implant according to the invention illustrating a first and second taper (the opposite side being identical in appearance);

FIG. 12 is a top plan view of the implant of FIG. 11 taken 90° from the view of FIG. 11 (the opposite side being identical in appearance);

FIG. 13 is a side elevation view of another embodiment of an implant according to the invention having a first and second taper;

FIG. 14 is an end view of two opposing vertebrae stretched apart and including two implants of FIGS. 1–5 disposed therebetween;

FIG. 15 is a side elevation view of an insertion tool for use with an implant of invention;

FIG. 17 is perspective view of an implant of FIGS. 1–5 and the distal end of the insertion tool of FIG. 15;

FIG. 20 is an end on view of an implant of FIGS. 1–5 loaded onto the distal end of the insertion tool of FIG. 19.

DETAILED DESCRIPTION OF THE INVENTION

Figure 1:
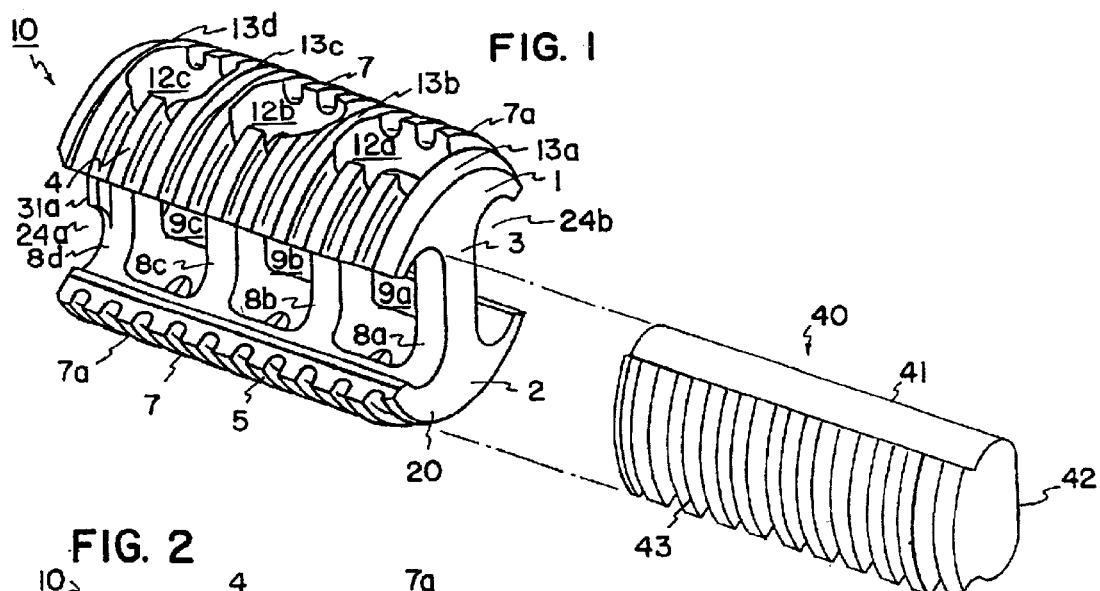
FIG. 1 is a perspective view of an implant embodiment of the invention having a first and second curved bearing surfaces.

The present invention is directed to intervertebral stabilization and arthrodesis procedures that can provide for greater structural integrity of the bony union between fused vertebral bodies of the vertebral column. In addition, the devices and methods disclosed herein facilitate greater continuity between the bone formed at the fusion site and the remainder of the vertebral body. In some embodiments, the invention provides enhanced ability to assess new bone growth during the fusion process using typical diagnostic imaging modalities such as x-rays.

An implant of the invention can be prepared from known implant materials including, for example, titanium, stainless steel, porous titanium, bone or other suitable material used to manufacture orthopedic implants. Unlike prior implants, the present implants have no surrounding sidewalls and no chamber. The disclosed implants support the axial load of the vertebral column by a "central support member" that separates opposing bearing surfaces of the implant.

The "central support member" provides for stabilization of the vertebral bodies with a reduced area of contact between the exterior surface of the implant and the inside surface of a bore formed to accommodate the implant. In addition to promoting greater structural integrity and continuity of the bony union, the reduced contact area also reduces obstruction of assessment of the fusion process. Further reduction in obstruction of assessment of the fusion process can be provided by forming openings in the bearing surfaces and/or providing the central support member in the form of one or more columns having openings in between.

In some embodiments, in comparison to prior implants, the present implants have a reduced displacement volume relative to the cylindrical bore size necessary for insertion of the implant. For example, in some embodiments, the displacement volume of the implant takes up about 10% to 40% of the bore volume necessary to accommodate the implant between opposing vertebrae. In one preferred embodiment, the implant takes up about 24% or less of the bore volume necessary to accommodate the implant. Thus, in this embodiment, the remaining 76% of the bore volume can be filled with bone or other suitable bone support matrix. In contrast, the BAK implant (U.S. Pat. No. 5,489,308), commercially available from Sulzer Spine-Tech, Inc., takes up about 41% of the bore volume on a relative basis and the Proximity implant (U.S. Pat. No. 5,609,636), also available from Sulzer Spine-Tech, Inc., takes up about 30% of the bore volume on a relative basis.

According to the invention, the central support member is located between the bearing surfaces of the implant and typically does not extend to the lateral edges of the bearing surfaces. The term "central" includes an implant having a support member located away from the exact center of the bearing surfaces but providing the same function of a herein described centrally located support member. The "bearing surfaces" are the surfaces of the implant that directly contact the opposing vertebral bodies. The "lateral edges" of the bearing surfaces are the lateral most aspects of the bearing surfaces.

The implants also have a leading end and trailing end that are spaced apart along the longitudinal axis of the implant. In general, a transverse cross section taken through the longitudinal axis of the present implants has a substantially "I" shaped configuration. The "central support member" forms the vertical arm of the "I" and the "transverse members" form horizontal arms defining the free ends of the "I". In use, the central support member is typically oriented parallel to the longitudinal axis of the vertebral column and the transverse members are oriented perpendicular.

Each transverse member has a peripheral surface that is in direct contact with one of the opposing vertebral bodies. The transverse members also have an inner surface that is continuous with the lateral aspect of the central support member. A "channel" is present on either side of the central support member within the inner surface of the transverse member. As will be appreciated from the illustrated embodiment, the channel extends through the leading and trailing ends of the implant and opens laterally between opposing transverse members. As discussed below, after insertion of the implant between opposing vertebrae, the channel can be filled with a bone support matrix to facilitate new bone growth.

In some embodiments, the bearing surfaces are curved to provide an external surface configured for insertion of the implant into a circular bore formed between opposing vertebrae. In such embodiments, the opposing bearing surfaces can be parallel to one another along the longitudinal dimension of the implant from the trailing end to leading end. Alternatively, the implant can include a single or double taper including at least a first taper diverging from the longitudinal axis of the implant from the leading end to the trailing end. Implant embodiments having curved bearing surfaces can include a pattern for anchoring the implant between opposing vertebrae. The pattern can be, for example, knurls or other intermittently raised surface. Alternatively, the pattern can be a portion of a helical thread pattern which resists displacement of the implant from an insertion bore and also provides for threaded insertion of the implant into the bore.

In other embodiments, the bearing surfaces can be substantially linear. According to this embodiment, preferably, at least one of the bearing surfaces includes a pattern for anchoring the implant and reducing the chance of displacement of the implant from of the insertion bore.

The invention also provides a kit comprising a plurality of incrementally sized implants which can be selected by the clinician based on the size needed for a particular patient. In other embodiments kits are provided which include instrumentation for performing an implant procedure with or without a plurality of incrementally sized implants.

Instruments and methods suitable for insertion of an implant of the invention are disclosed in, for example, U.S. Pat. Nos. 5,489,308 and 5,458,638, and co-pending application U.S. Ser. Nos. 08/902,083 and 08/921,001, the entire disclosures of which are incorporated herein by reference. Additional instruments particularly advantageous for the implants disclosed herein are described in detail below.

After the implant is inserted into the bore, the volume of the bore not occupied by the implant, for example in the region of the channels, can be filled with a bone support matrix. As used herein, a "bone support matrix" is a material that facilitates new bone growth between the opposing vertebral bodies. Suitable bone support matrices can be resorbable or nonresorbable and osteoconductive or osteoinductive. Examples of suitable matrices according to the invention include synthetic materials, such as Healous™, available from Orquest, Mountain View, Calif. NeOsteo™, available from Sulzer Orthopedic Biologics, Denver, Colo. or any of a variety of bone morphogenic proteins (BMPs). Suitable bone support matrices also include heterologous, homologous, or autologous bone and derivatives thereof. Preferably, the bone support matrix is radiolucent on x-rays.

The bone support matrix can be packed into the bore after insertion of the implant between the vertebral bodies. Alternatively, a bone support matrix can be configured to fit into the longitudinal channels on either side of the central support member before or after installation of the implant into the site of implantation. In one embodiment, the external surface of the bone support matrix can include a portion of a helical thread. According to this embodiment, when used with an implant having a portion of helical threads on a bearing surface, the helical threads of the bone matrix can be complimentary to the helical threads on the implant such that when placed into the channel a complete helical thread pattern is formed for threadedly inserting the implant into the prepared site.

DETAILED DESCRIPTION OF THE ILLUSTRATED EMBODIMENTS

The implants and instruments of the invention will now be described by reference to the several drawing figures. The illustrated embodiments are provided only for descriptive purposes and are not intended to limit the implants which are within the scope of the invention. It will be appreciated, however, that while the illustrated embodiments share the general configuration of an "I" in transverse cross section, each embodiment has additional unique and advantageous features.

A. Implants

FIGS. 1–5 illustrate a first embodiment of an implant of the invention having a first transverse member 1 and a second transverse member 2 spaced apart by a central support member 3. When inserted between opposing vertebrae, each transverse member is oriented transverse to the longitudinal axis of the vertebral column and the central support member is oriented parallel to the longitudinal axis of the vertebral column. Thus, the transverse members can also be referred to as a "cranial transverse member" and a "caudal transverse member" to indicate that when inserted between opposing vertebrae, one transverse member is oriented cranially and the other transverse member is oriented caudally.

The first transverse member 1 has a first bearing surface 4 and the second transverse member 2 has a second bearing surface 5. The first bearing surface 4 and the second bearing surface 5 include a pattern 7 for anchoring the implant within an insertion bore. The illustrated pattern 7 is a portion of a helical thread 7a which provides for threadedly inserting implant 10 into a bore prepared between opposing vertebrae. The helical thread 7a is generally rectangular in profile. However, a thread pattern having sharp surfaces or a combination of rectangular and sharp threads can be used. In addition, other surface patterns, such as knurls, could be provided on the bearing surface and the device implanted by impact into a bore.

The illustrated central support member 3 comprises a plurality of columns 8a–8d with openings 9a–9c therebetween. Columns 8a–8d of central support member 3 maintain transverse members 1 and 2 in a fixed spatial relationship and provide rigid support and stabilization of opposing vertebral bodies which contact bearing surfaces 4 and 5. Openings 9a–9c between columns 8a–8d promote greater continuity of new bone growth through the central support member as well as reduce the presence of radiopaque material which can obstruct assessment of the fusion process using typical diagnostic imaging modalities.

Figure 3:
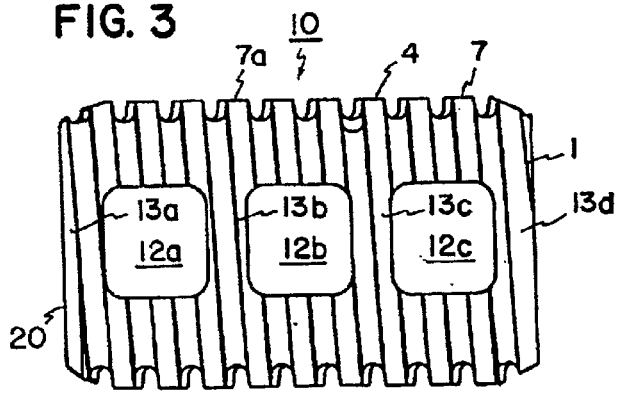
FIG. 3 is a top plan view of a first transverse member of the implant of FIG. 1 (the top view of the second transverse member view being identical in appearance)

FIG. 3 illustrates a top view of the bearing surface 4 of the first transverse member 1. Rotation of the implant 180° would show the bearing surface 5 of the second transverse member 2 which is substantially identical in appearance. The bearing surface 4 (and 5) includes rigid transverse supports, or trusses, 13a–13d having openings 12a–12c therebetween. As illustrated, the portion of helical thread 7a can be continuous in the region of the transverse supports 13a–13d. In addition to facilitating greater structural integrity of the bony union, the openings 12a–12d also enhance the ability to assess new bone formation during the fusion process.

Figure 4:
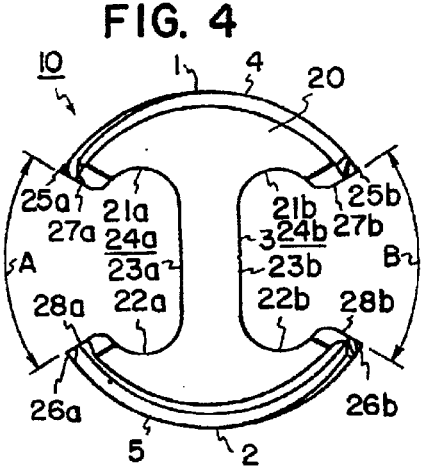
FIG. 4 is an elevation view of a trailing end of the implant of FIG. 1.

FIG. 4 is an elevation view of the trailing end 20 of implant 10. The inner surfaces 21a, 21b of transverse member 1 oppose the inner surfaces 22a, 22b of transverse member 2. The inner surfaces of the transverse members are continuous with the lateral surfaces 23a, 23b of the central support member 3. On either side of the central support member 3, there are two longitudinal channels 24a and 24b. Channel 24a is defined by surfaces 21a, 22a and 23a and channel 24b is defined by surfaces 21b, 22b and 23b. Channels 24a and 24b not only provide a large area for uninterrupted new bone growth around the implant, but they also provide an arrangement for attachment of an insertion tool described below.

Between each inner surface 21a, 22a, 21b and 22b and its respective lateral edge 25a, 26a, 25b and 26b of transverse members 1 and 2, there are undercut segments 27a, 28a, 27b and 28b. The angle A between undercut segments 27a and 28a and the angle B between undercut segments 27b and 28b can be different. As will be discussed below, asymmetry of angles A and B can provide for proper orientation of the helical threads 7a of implant 10 with complimentary threads of a below described insertion tool.

Figure 5:
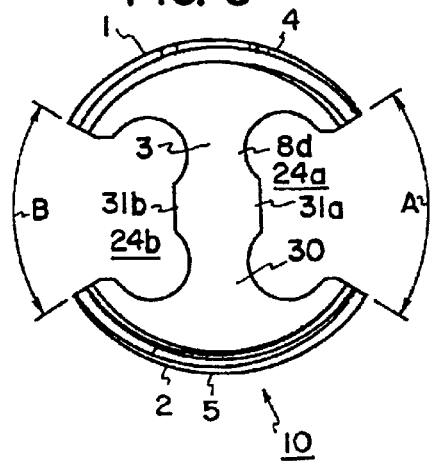
FIG. 5 is an elevation view of a leading end of the implant of FIG. 1.

FIG. 5 is an elevation view of the leading end 30 of implant 10. In the illustrated embodiment, trailing column 8d of central support member 3 includes lateral tabs 31a and 31b. Lateral tabs 31a and 31b render the leading end distinguishable from the trailing end such that implant 10 can only be loaded onto a below described implant insertion tool in a certain orientation.

Figure 2:
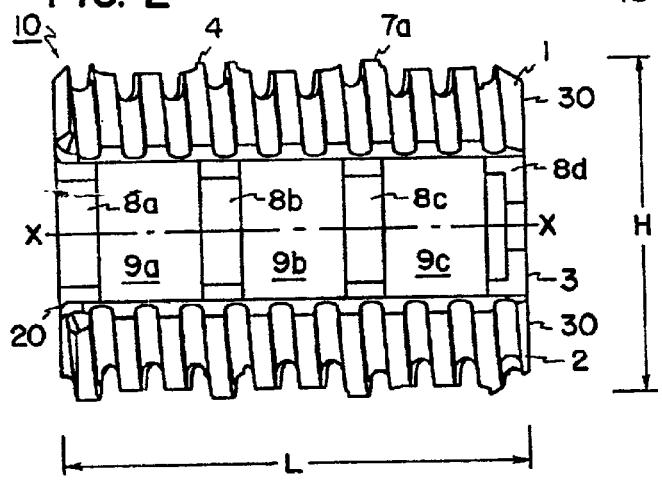
FIG. 2 is a side elevation view of the implant of FIG. 1 (the opposite side being identical in appearance)

Referring to FIG. 2, the leading end 30 and trailing end 20 are spaced apart along the longitudinal axis X—X of implant 10 to provide a length L. The implant 10 can be provided with different lengths L between leading end 30 and trailing end 20 as well as different heights H between the bearing surfaces 4 and 5 of transverse members 1 and 2, respectively. Incrementally sized length and height implants 10 can be provided in a kit for selected use by the surgeon based on the particular patient's needs.

Once inserted into a prepared bore site, the channels 24a, 24b and any other area of the bore not occupied by the implant can be filled with a bone support matrix. Referring again to FIG. 1, one embodiment of a bone support matrix 40 is illustrated. According to this embodiment, the bone support matrix 40 can be a resorbable matrix 41 configured to fit within channels 24a or 24b. The inner surface 42 of bone support matrix 40 can be shaped to follow the contours of channels 24a or 24b. The outer surface 43 of bone support matrix 40 can include a portion of helical threads 43 which are complimentary to portions of helical threads 7a of implant 10. According to this embodiment, the implant 10 can be threaded into a tapped insertion bore with bone support matrix 40 in place. In alternative embodiments, after placement of the implant 10 into a bore, a bone support matrix configured to follow the contours of channels 24a and 24b but without a threaded outer surface can be inserted into the channels 24a and 24b of the implant.

Figure 6:
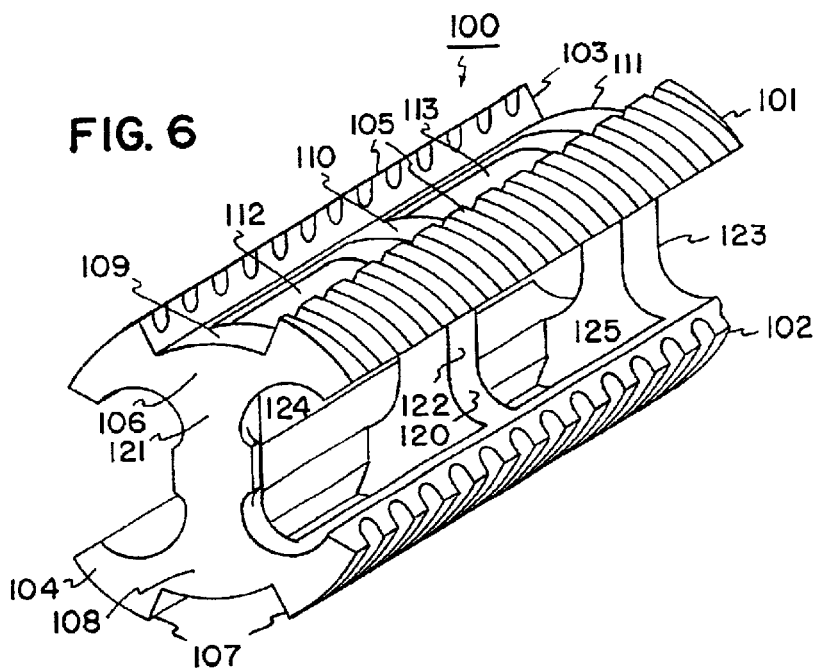
FIG. 6 is a perspective view of a second embodiment of an implant according to the invention.
Figure 7:
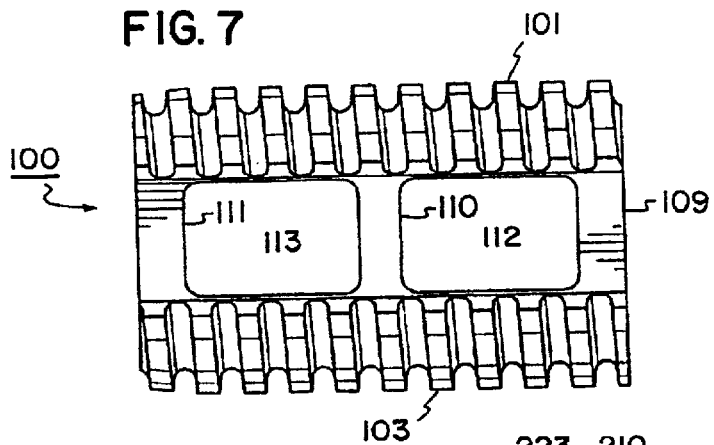
FIG. 7 is a top plan view of a first transverse member of the implant of FIG. 6 (the top view of the second transverse member being identical in appearance)

Referring now to FIGS. 6–7, a second embodiment of an implant 100 is illustrated. The implant 100 includes four generally linear thread segments 101, 102, 103 and 104. Linear thread segments 101 and 103 provide a bearing surface 105 of a first transverse member 106 and linear thread segments 102 and 104 provide a bearing surface 107 of a second transverse member 108. As illustrated best in the top view of FIG. 7, thread segments 101 and 103 (and 102 and 104) are maintained in spaced apart alignment by transverse supports 109, 110 and 111. In the illustrated embodiment there are two openings 112 and 113 between transverse supports 109, 110 and 111. (The relative arrangement of the second transverse member 108 having thread segments 102 and 104 is identical to that just described for the first transverse segment 106). Transverse members 106 and 108 are maintained in spaced apart alignment by central support member 120. In the illustrated embodiment, central support member 120 comprises columns 121, 122 and 123 and has openings 124 and 125 therebetween.

It will be appreciated that the transverse members and central support member of an implant need not include any openings as described thus far. In addition, rather than comprising support columns, and openings as illustrated, the central support member can include several fine thickness support columns with several fine openings interspersed therebetween giving a profile appearance similar to the tines of a comb. A similar arrangement can be provided for the transverse members rather than having the trusses and openings illustrated.

Figure 8:
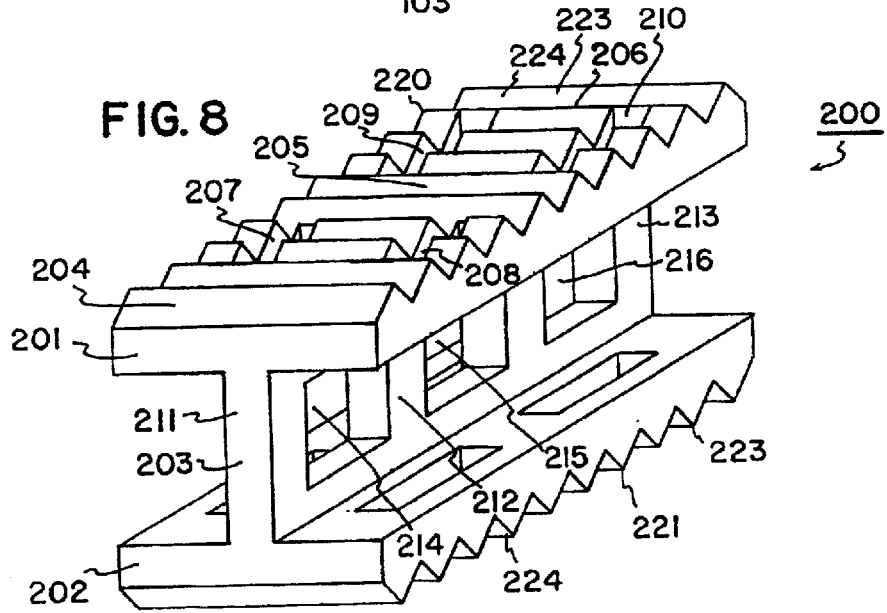
FIG. 8 is a perspective view of a third embodiment of an implant according to the invention.

Referring now to FIG. 8, another implant 200 is illustrated. Implant 200 has a more classic "I-beam" appearance in cross section. Similar to the previously discussed embodiments, first transverse member 201 and second transverse member 202 are maintained in spaced apart alignment by central support member 203. Transverse member 201 also includes transverse supports 204, 205 and 206 having openings 207–210 therebetween. Transverse member 202 has an identical arrangement of transverse supports and openings. In the illustration, central support member 203 comprises columns 211, 212, and 213 has openings 214–216 therebetween. Bearing surfaces 220 and 221 include a pattern 223 of intermittent raised edges 224 which reduce the chance of displacement of the implant 200 once inserted into a bore.

It should be noted that as an alternative to the helical threads present on the bearing surface of other implants described herein, a pattern such as intermittent raised surface 224 or other non-helical thread pattern can be present on the bearing surface. Thus, rather than threadedly inserting such an implant into an insertion bore, the implant can simply be impacted by driving it into the bore along the X—X axis of the implant.

Figure 9:
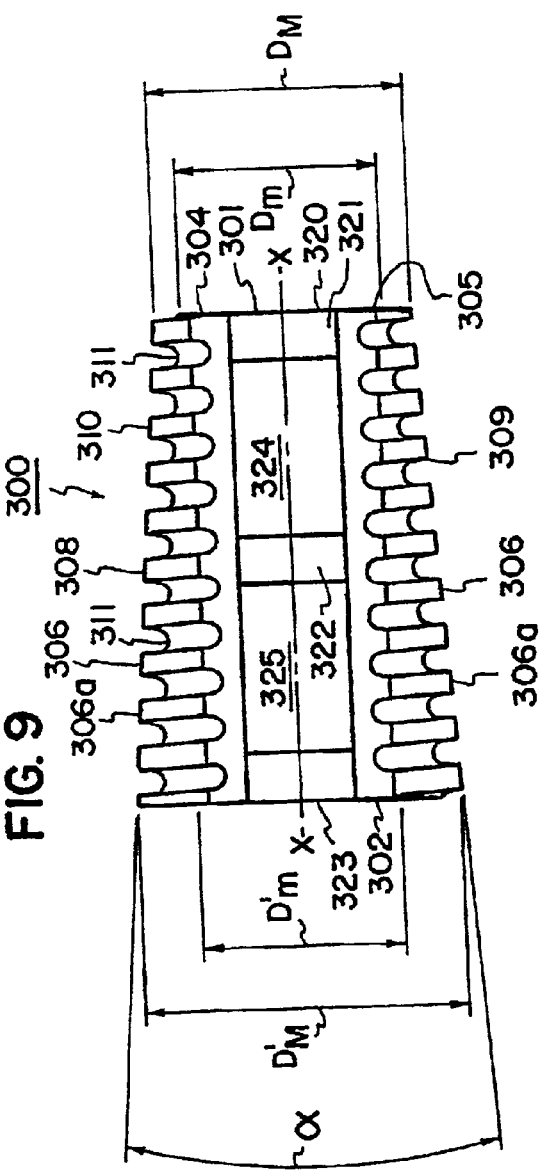
FIG. 9 is a side elevation view of an embodiment of a tapered implant according to the invention (the opposite side being identical in appearance)
Figure 10:
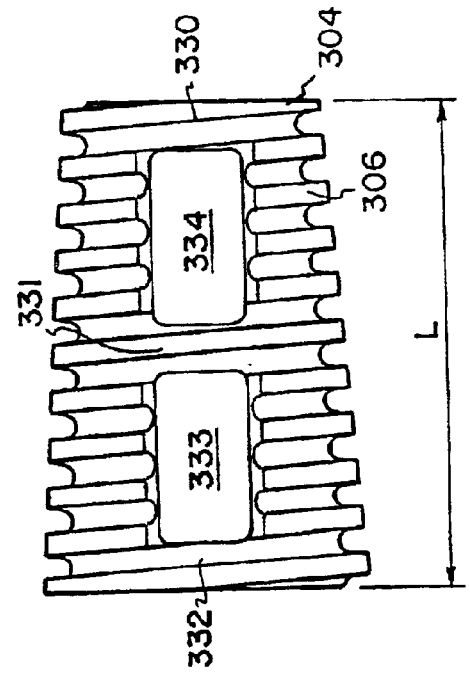
FIG. 10 is a top plan view of the implant of FIG. 9 taken 90° from the view of FIG. 9 (the opposite side being identical in appearance)

FIGS. 9 and 10 illustrate an implant 300 having a first taper diverging from longitudinal axis X—X from leading end 301 to trailing end 302. In the side view of FIG. 9, implant 300 has a substantially frusto-conical shape with a conical angle α equal to a desired lordosis between the vertebrae into which the implant 300 is to be placed as fully described in co-pending application U.S. Ser. No. 08/902,083, the entire disclosure of which is incorporated herein by reference. In the illustrated embodiment, angle α is 8°. However, it will be appreciated that as with other implants, implant 300 will be available in a wide variety of sizes. For example, such implants may be provided having angles α ranging from 1° to 20° in 1° increments to permit a physician to select a desired implant to attain a desired lordosis. Further, such implants can be provided in varying heights (i.e., the diameter of the implants) to accommodate desired distraction and lordosis between opposing vertebrae.

The first transverse member 304 and second transverse member 305 include a surface pattern 306 comprising a portion of helical threads 306a along first bearing surface 308 and second bearing surface 309. The threads 306a are generally square in cross-section with their flat outer peripheral surfaces 310 set at an angle of one-half α with respect to the longitudinal axis X—X and defined valleys 311 between the threads 306a. At the leading end 301, the implant has a major diameter DM measured between diametrically opposite outer radial surfaces 310 of the threads 306a at the leading end 301. At the leading end 301, the implant 300 has a minor diameter $D_M$ measured as the distance across the implant 300 between the valleys 311 of the thread pattern 306a At the trailing end 302, the implant 300 has a major diameter $D'_M$ measured between diametrically opposite outer radial surfaces 310 of threads 306a at the trailing end 302. Finally, at the trailing end 302, the implant 300 has a minor diameter $D'_m$ measured between diametrically opposite valleys 311 at the trailing end 302.

The central support member 320 of implant 300 comprises vertical columns 321, 322 and 323 including openings 324 and 325 therebetween. Referring to the top view of FIG. 10, it can be seen that the first transverse member 304 (and also second transverse member 305) include transverse supports 330, 331 and 332 and include openings 333 and 334 therebetween. As with all implants disclosed herein, the number of columns and transverse supports can vary. The objective being to provide rigid support with the greatest amount of free space.

Referring to FIGS. 11–13, another embodiment of an implant 400 is shown. According to this embodiment, the first transverse member 401 and second transverse member 402 are maintained in spaced apart relationship by central support member 403. Central support member 403 includes columns 420, 421 and 422 with openings 423 and 424 therebetween. First transverse member 401 includes transverse supports 425, 426 and 427 with openings 428 and 429 therebetween. The second transverse member 402 has an identical arrangement.

Implant 400 has a first and second taper and a longitudinal axis X—X extending from a leading end 404 to a trailing end 405. The trailing end 405 of the present embodiment comprises a "trailing end rise" (TER) 406 and a terminal end 407. The first taper of implant 400 diverges from the axis from the leading end 404 to the trailing end rise 406 of the trailing end 405. The second taper diverges from the axis from the terminal end 407 to the TER 406. The trailing end rise 406 is the region of greatest diameter of the implant 400.

The first taper provides the bi-tapered implant 400 with a substantially frusto-conical shape with a conical angle α equal to a desired lordosis between selected vertebrae. The angle α of the illustrated embodiment, measured from the leading end 404 to the TER 406 is 8°, however, as previously stated, the herein disclosed implants will be available with a variety of angles and sizes. Referring to FIG. 11, the leading end 404 has a major diameter $D_M$ measured between diametrically opposite outer radial surfaces 410 of the threads 411 at the leading end 404. The leading end 404 also has a minor diameter $D_m$ measured between diametrically opposite inner radial surfaces 412 of the valleys 413 of the thread pattern 411 of implant 400.

At the trailing end 405, the implant 400 has a major diameter $D'_M$ measured between diametrically opposite outer radial surfaces 414 of the threads 411 at the trailing end rise 406. The trailing end 405 also has a minor diameter $D'_m$ measured across terminal end 407.

The second taper of the implant 400 has a second angle, δ, extending from the terminal end 407 to the TER 406. The angle δ will vary with the diameter $D'_M$ of the TER 406, the diameter $D'_m$ of the terminal end 407, and the longitudinal distance $L_E$ therebetween. In the illustrated embodiment, the diameter $D'_m$ of the terminal end 407 is equal to the major diameter $D_M$ of the leading end 404.

The longitudinal distance $L_E$ can be about 5% to 25% of the overall length L of the implant. Generally, $L_E$ is less than 15% of the overall length L, typically about 8–10%.

It will be appreciated that the slope "m" of the second taper, relative to the longitudinal axis X—X, can be calculated by the equation:

$$D'_M - D'_m / L_E$$

In the illustrated embodiment, m is about 1 (45°). However, the actual slope dimensions m can vary, typically, between 0.58 (30°) and 1.73 (60°).

The helical threads 411 can extend along the second taper as illustrated at 415 of FIGS. 11–12. Alternatively, as illustrated in FIG. 13, the threads 411 can stop at the terminal end rise 406 and the second taper comprise a flat 416, undulating or other non-threaded surface, from trailing end rise 406 to terminal end 407.

Implant 400 can also include other features as previously described for an implant.

B. Instrumentation and Insertion

Instrumentation and methods for preparing an insertion bore for placement of an implant between opposing vertebrae are known. U.S. Pat. Nos. 5,458,638 and 5,489,308 and co-pending applications U.S. Ser. Nos. 08/921,001 and 09/036,165 (M&G Docket No. 6683.22USI1 filed Mar. 6, 1998) describe preferred instrumentation and methods for preparing an implant bore and inserting an implant therein. The methods include the use of a distraction spacer, boring tools and tapping tools. In addition, copending U.S. Ser. Nos. 08/902,083, 08/902,407 and 08/902,431 disclose distraction spacers, boring tools and tapping tools for preparing a tapered insertion bore suitable for insertion of single tapered implant 300 or double tapered implant 400. The disclosure of each of these patents and patent applications are incorporated herein by reference.

FIG. 14 diagrammatically illustrates two implants 10 inserted into a threaded bore between opposing vertebral bodies 450, 451. It should be noted that in a preferred method, the openings 12a–12c of implants 10 are beyond the cortical end plates 452, 453 and provide exposure to cancellous bone 454, 455. A bone support matrix can be packed around the implants 10.

FIGS. 15–18 illustrate one preferred insertion tool 500. Insertion tool 500 includes a tool body 502 extending from a proximal end 504 to a distal end 506. In the illustrated embodiment, an internal bore 508 extends completely through the tool from the proximal end 504 to the distal end 506. At the proximal end 504, the bore can be provided with internal threads 510. A handle 508 is provided at the proximal end 504 to permit a surgeon to manipulate the tool 500.

Figure 16:
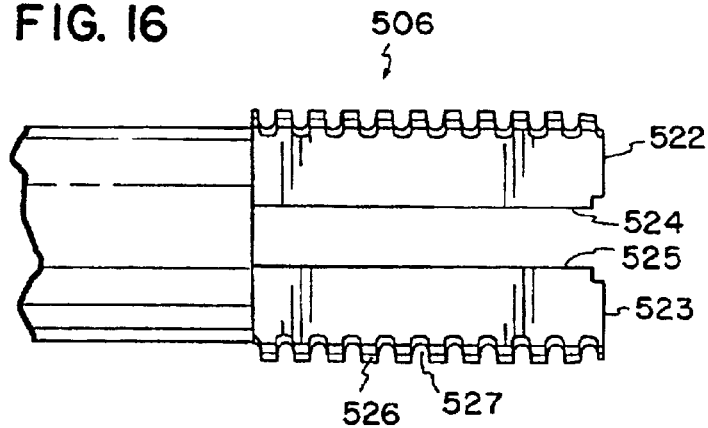
FIG. 16 is a side view of a distal end of the insertion tool of FIG. 15.

At the distal end 506, a plurality of grips are provided as best illustrated in FIGS. 16 and 17. The grips include threaded grips 522, 523. The threaded grips 522, 523 have opposing interior surfaces 524, 525 configured to slide into channels 24a and 24b of implant 10. The exterior surfaces of the grips 522, 523 are provided with threads 526 and valleys 527 which are complimentary to helical thread portions 7a of the implant 10.

FIG. 17 illustrates a perspective view of implant 10 and the distal end 506 of insertion tool 500. The thread pattern 526 of the threaded grips 522, 523 matches the helical thread pattern of the threaded portions 7a of the implant 10 to define a generally continuous thread pattern through the combination of the implant 10 and the tool 500.

Figure 18:
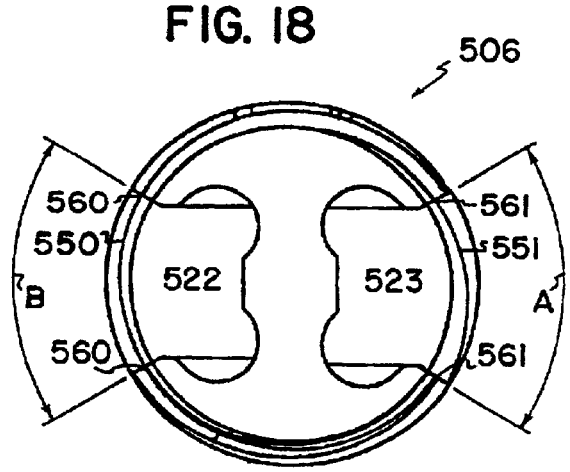
FIG. 18 is an end on view of the distal end of the insertion tool of FIG. 15 with an implant of FIGS. 1–5;.

Referring now to the distal end view of tool 500 in FIG. 18 a preferred feature for assuring thread alignment between an implant 10 and insertion tool 500 is described. As illustrated, the lateral aspects 550 and 551 of each gripper 522 and 523, respectively, each include a pair of tapered ridges 560 and 561. The angle A formed between tapered ridges 561 is different than the angle B formed between tapered ridges 560. However, angle A between tapered ridges 561 is identical to angle A of implant 10 and angle B of tapered ridges 560 is identical to angle B of implant 10 (see FIG. 5). Thus, by providing different angles A and B on the distal end 506 of tool 500 which match with angles A and B of implant 10 only in a particular orientation, proper alignment of thread portions 7a of implant 10 and threads 526 of tool 500 is assured for proper insertion of the implant into a tapped insertion bore. In the illustrated embodiment, the opposing interior surfaces 524, 525 of the distal end 506 of grips 522 and 523 also include notches 570a and 570b which receive tabs 31a and 31b of implant 10, respectively.

Figure 19:
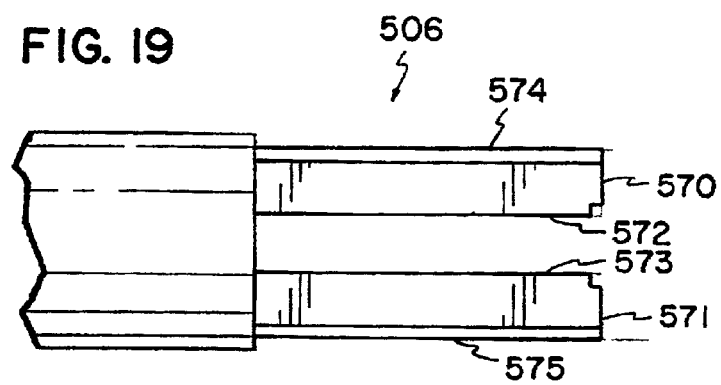
FIG. 19 is a side elevation view of an alternative embodiment of an insertion tool according to the invention.

Referring now to FIGS. 19 and 20, an alternative embodiment of the distal end 506 of a tool 500 is illustrated. According to this embodiment, unthreaded grips 570 and 571 have opposing interior surfaces 572, 573 that provide for sliding grips 570 and 571 into channels 24a and 24b of implant 10. However, as visualized best in FIG. 20, the lateral aspects 574, 575 of grips 570, 571, respectively, do not include threads and do not extend to the lateral edges 25a, 25b, 26a and 26b of implant 10.

The insertion tool 500, with threaded or unthreaded grips as just described, can also to include two additional grips that slide into the regions between thread segments 101 and 103 and 102 and 104 of implant embodiment 100. Such additional grips are illustrated, for example, in FIGS. 24, 27, 28 and 31 of co-assigned U.S. Pat. No. 5,609,636, the entire disclosure of which is incorporated herein by reference.

Finally, an insertion tool as described above can also be prepared for tapered implants 300 and 400. The difference being that grips 522 and 523 or 570 and 571 are tapered from the proximal end to the distal end as disclosed in co-pending application U.S. Ser. No. 08/902,083.

Having now described the present invention, it will be apparent to one of ordinary skill in the art that many changes and modifications can be made in the invention without departing from the spirit or scope of the appended claims.

I claim:

1. An implant for intervertebral fusion between opposing vertebrae, said implant comprising:
    an implant body having a first end and a second end spaced along a longitudinal axis of the body, said first end having a first diameter and said second end having a second diameter wherein the, second diameter is larger than the first diameter; and
    said implant body comprising first and second load bearing surfaces extending between the first and second ends of the implant body and being spaced apart by a central support member, the central support member having a width narrower than a width of the first and second load bearing surfaces, wherein the width of the first and second load bearing surfaces extends between the first and second ends of the implant body, wherein the central support member is coextensive with a midline of the implant body extending along the longitudinal axis, wherein said body is substantially "I" shaped in cross-section.

2. The implant of claim 1, wherein said first and second load bearing surfaces are non-continuous.

3. The implant of claim 1, wherein said body is tapered at least at said first end.

4. The implant of claim 1, wherein a distance between the first and second load bearing surfaces varies along the longitudinal axis.

5. The implant of claim 1, wherein the diameter of the second end is greater than a diameter of the implant at least one other point along the longitudinal axis.

6. The implant of claim 1, wherein said first and second load bearing surfaces taper toward one another from said second end to said first end.

7. The implant of claim 6, wherein said body tapers at an angle of 80°.

8. The implant of claim 1, wherein said first and second load bearing surfaces include portions of a helical thread pattern.

9. The implant of claim 1, wherein said first and second load bearing surfaces include a pattern for anchoring to a vertebral body.

10. The implant of claim 1, wherein said central support member extends from said first end to said second end of said implant.

11. The implant of claim 10, wherein said central support member includes at least one opening therethrough.

12. The implant of claim 1, wherein said central support member comprises a plurality of columns.

13. The implant of claim 1, wherein said central support member passes through a single plane between diametrically opposed regions of said first and second load bearing surfaces.

14. An implant for intervertebral fusion between opposing vertebrae, said implant comprising:
    an implant body having a first end and a second end, said body having first and second load bearing surfaces extending along a longitudinal axis of the body from the first end to the second end, the first acid second load bearing surfaces having a width extending perpendicular to the longitudinal axis, said first and second load bearing surfaces having a midline extending along the longitudinal axis, said first and second load bearing surfaces being spaced apart by a first height at the first end and a second height at the second end, wherein the first height is less than the second height; and
    said implant body comprising a plurality of columns connecting the first and second load bearing surfaces along their midlines, the columns having a width narrower than the width of the first and second load bearing surfaces, wherein the columns of the plurality of columns are aligned one behind another at the longitudinal axis.

15. The implant of claim 6, wherein the implant body has a continuous taper from the second end to the first end.

16. The implant of claim 1, wherein said first and second load bearing surfaces form open channels on each side of the central support member, extending from the first end of the implant body to the second end of the implant body.

17. The implant of claim 14, wherein, said first and second load bearing surfaces include portions of a helical thread pattern.

18. The implant of claim 17, wherein said first and second load bearing surfaces are threaded from the first end of the body to the second end of the body.

19. An implant for intervertebral fusion between opposing vertebrae, said implant comprising:
    an implant body having a first end and a second end spaced along a longitudinal axis of the body, said first end having a first diameter and said second end having a second diameter wherein the second diameter is larger than the first diameter; and
    said implant body comprising first and second load bearing surfaces extending between the first and second ends of the implant body and being spaced apart by a central support member, wherein the first and second load bearing surfaces taper toward one another from said second end to said first end;
    said central support member having a width narrower than a width of the first and second load bearing surfaces, wherein the width of the first and second load bearing surfaces extends between the first and second ends of the implant body;
    said central support member being coextensive with a midline of the implant body extending along the longitudinal axis, wherein said body is substantially "I" shaped in cross-section, wherein said first and second load bearing surfaces form open channels on each side of the central support member, extending from the first end of the implant body to the second end of the implant body.

20. An implant for intervertebral fusion between opposing vertebrae, said implant comprising:
    an implant body having a first end and a second end, said body having first and second load bearing surfaces extending along a longitudinal axis of the body from the first end to the second end, the first and second load bearing surfaces having a width extending perpendicular to the longitudinal axis, said first and second load bearing surfaces having a midline extending along the longitudinal axis, said first and second load bearing surfaces being spaced apart by a first height at the first end and a second height at the second end, wherein the first height is less than the second height, wherein said first and second load bearing surfaces taper toward one another from said second end to said first end, said first and second load bearing surfaces including portions of a helical thread pattern;

said implant body comprising a central support member connecting the first and second load bearing surfaces along their midlines, the central support member having a width narrower than the width of the first and second load bearing surfaces; and said first and second load bearing surfaces having opposing inner surfaces forming open channels on each side of the central support member, extending from the first end of the implant body to the second end of the implant body.

21. An implant for intervertebral fusion between opposing vertebrae, said implant comprising:

an implant body having a first end and a second end, said body having first and second load bearing surfaces extending along a longitudinal axis of the body from the first end to the second end, the first aid second load bearing surfaces having a width extending perpendicular to the longitudinal axis, said first and second load bearing surfaces having a midline extending along the longitudinal axis; and said implant body comprising a plurality of columns connecting the first and second load bearing surfaces along their midlines, the columns having a width narrower than the width of the first and second load bearing surfaces, wherein the columns of the plurality of columns are aligned one behind another at the longitudinal axis.

22. The implant of claim 21, wherein said first and second load bearing surfaces have at least two openings.

23. The implant of claim 21, wherein said first and second load bearing surfaces have opposing inner surfaces forming open channels on each side of the columns.

* * * * *

UNITED STATES PATENT AND TRADEMARK OFFICE
CERTIFICATE OF CORRECTION

PATENT NO. : 6,855,166 B2
DATED : February 15, 2005
INVENTOR(S) : Douglas W. Kohrs It is certified that error appears in the above-identified patent and that said Letters Patent is hereby corrected as shown below:

Column 11,
Line 53, delete "80" and insert therefor -- 8 --

Column 12,
Line 6, delete "acid" and insert therefor -- and --

Column 14,
Line 4, delete "aid" and insert therefor -- and --

Signed and Sealed this

Twenty-fourth Day of May, 2005

JON W. DUDAS
*Director of the United States Patent and Trademark Office*